US00PP37714P2

(12) United States Plant Patent
Wagner

(10) Patent No.: US PP37,714 P2
(45) Date of Patent: Sep. 29, 2026

(54) BLUEBERRY PLANT NAMED 'OBG-18064'

(50) Latin Name: *Vaccinium corymbosum*
Varietal Denomination: OBG-18064

(71) Applicant: Robert Gabriel, Silverton, OR (US)

(72) Inventor: Adam L. Wagner, Brownsville, OR (US)

(73) Assignee: Robert Gabriel, Silverton, OR (US)

( * ) Notice: Subject to any disclaimer, the term of this patent is extended or adjusted under 35 U.S.C. 154(b) by 0 days.

(21) Appl. No.: 19/327,884

(22) Filed: Sep. 12, 2025

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC . A01H 5/08; A01H 5/00; A01H 6/368; A01H 6/36
See application file for complete search history.

(56) References Cited

PUBLICATIONS

Linkedin with Doug McCann retrieved online at https://www.linkedin.com/posts/doug-mccann-989a4949_here-is-a-new-northern-highbush-blueberry-activity-7221186482990989313-VhZ9#:~:text=Transcript-,Transcript,II%20chat%20with%20you%20soon., 3 pp. (Year: 2024).*

* cited by examiner

*Primary Examiner* — June Hwu
(74) *Attorney, Agent, or Firm* — Klarquist Sparkman, LLP

(57) ABSTRACT

A new and distinct blueberry plant variety named 'OBG-18064' is disclosed, characterized by its high yield of about 10 kg per plant, large firm fruit, which is about 4.3 g with a firmness of 241.9 g/mm$^3$, medium powder-blue color or bloom on the berry, and good flavor and shelf-life.

3 Drawing Sheets

Specification includes a Sequence Listing.

Latin name of the genus and species: *Vaccinium corymbosum.*
Variety denomination: 'OBG-18064'.

INCORPORATION OF ELECTRONIC SEQUENCE LISTING

The Sequence Listing is submitted as an XML file named "Sequence.xml," created on Sep. 8, 2025 (16,458 bytes), which is incorporated herein by reference.

BACKGROUND

The present disclosure relates to a new and distinct variety of highbush blueberry, or *Vaccinium corymbosum*, named 'OBG-18064'. *Vaccinium corymbosum* is of the family Ericaceae. The new *Vaccinium corymbosum* 'OBG-18064' was first identified in a cultivated area in Silverton, Oregon, USA.

SUMMARY

The new variety, 'OBG-18064', is the product of an open pollination of 'Bluecrop' (female parent, unpatented). The new variety is late mid-season, has large berries with good flavor, has no notable disease or other pest susceptibility beyond those also common for other blueberry varieties, and has a chilling requirement of approximately 800-1000 hours below 45° F. 'OBG-18064' has been asexually propagated (by vegetative cuttings) in Silverton, Oregon, USA, where it was also established for testing and comparison to industry standards.

The following traits have been repeatedly observed and are determined to be the unique and distinguishing characteristics of 'OBG-18064'. In combination, the following traits set the new variety apart from all other existing varieties of highbush blueberry known to the inventor:

1. High yield of about 10 kg per plant
2. Large fruit weighing about 4.30 g
3. Firm texture of about 241.90 g/mm$^3$
4. Medium powder-blue color or bloom on the berry In trials for the new variety in Silverton, Oregon, USA, standards 'Calypso' (U.S. Plant Pat. No. 25,995P3) and 'Legacy' (unpatented) were chosen for comparison as the most similar commercially available varieties. The parent 'Bluecrop' was introduced to the market in 1941 and today is most often grown for the processed fruit market. In comparison to 'OBG-18064', 'Bluecrop' tends to produce smaller fruit (approx. 14 mm) that is less firm (less than 200 g/mm$^3$) and has a lower yield of approximately 12 lbs per plant (about 5.4 kg). Since it is no longer competitive with newer varieties, it was not included as a standard for trial comparisons for 'OBG-18064'.

Table 1 below compares certain characteristics of 'OBG-18064' to 'Calypso' and 'Legacy'. The 'Legacy' variety was introduced to the market in 1993 and 'Calypso' was introduced in 2015. While 'Legacy' has remained popular amongst commercial growers, its popularity has been more due to familiarity and consistent yield rather than berry quality. The berry flavor tends to be flat and the fruit is small and soft. 'Calypso' improved the berry characteristics over 'Legacy' but its yield is only marginally better. 'OBG- 18064' represents an improvement over 'Calypso' in berry weight, berry diameter, and plant yield.

TABLE 1

Comparison of 'OBG-18064' to two commercial varieties.

| | 'OBG-18064' | 'Legacy' | 'Calypso' |
|---|---|---|---|
| Avg. Berry Weight | 4.30 | 3.0 | 3.8 |
| Avg. Berry Diameter (mm) | 20.80 | 17.4 | 19.8 |
| Berry Firmness (g/mm$^3$) | 241.90 | 218.0 | 280.4 |
| Over 4 Weeks | | | |
| Titratable Acidity (% CA) | 5.9 | 2.0 | 4.0 |
| Avg. Soluble Solids (%) | 13.0 | 14.7 | 12.5 |
| Avg. pH | 3.4 | 4.2 | 3.6 |
| Yield per Mature Plant (kg) | 10 | 6 | 7 |
| Berry Quality After 4 Weeks* | 5 | 3 | 3 |

*Subjective measure on a scale of 1 (lowest) to 5 (highest) reflecting appearance of mold, shrivel, adherence to fresh-picked fruit color and bloom.

The key improvements of 'OBG-18064' include:

Larger berry size and weight

Better flavor due to more pleasing aromatics and sugar/acid balance

42% (67%) yield improvement over 'Calypso' ('Legacy')

'OBG-18064' in an exceptional and unique new variety that will benefit the commercial blueberry industry. The plant can be machine harvested and the fruit quality is acceptable for the fresh, frozen or pureed blueberry market.

Figure 1:
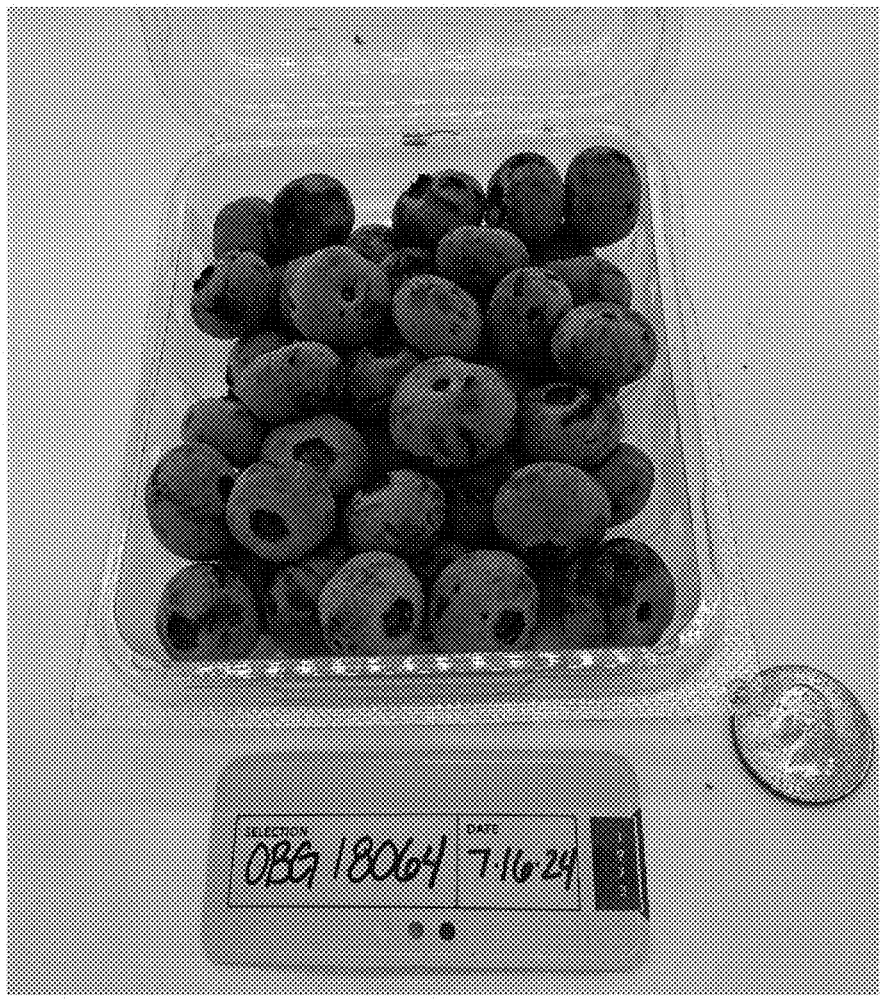
FIG. 1 is a photograph showing a close-up of 'OBG-18064' fruit in a packing clam shell. This photo was taken under artificial light in a photo tent on Jul. 16, 2024.
Figure 2:
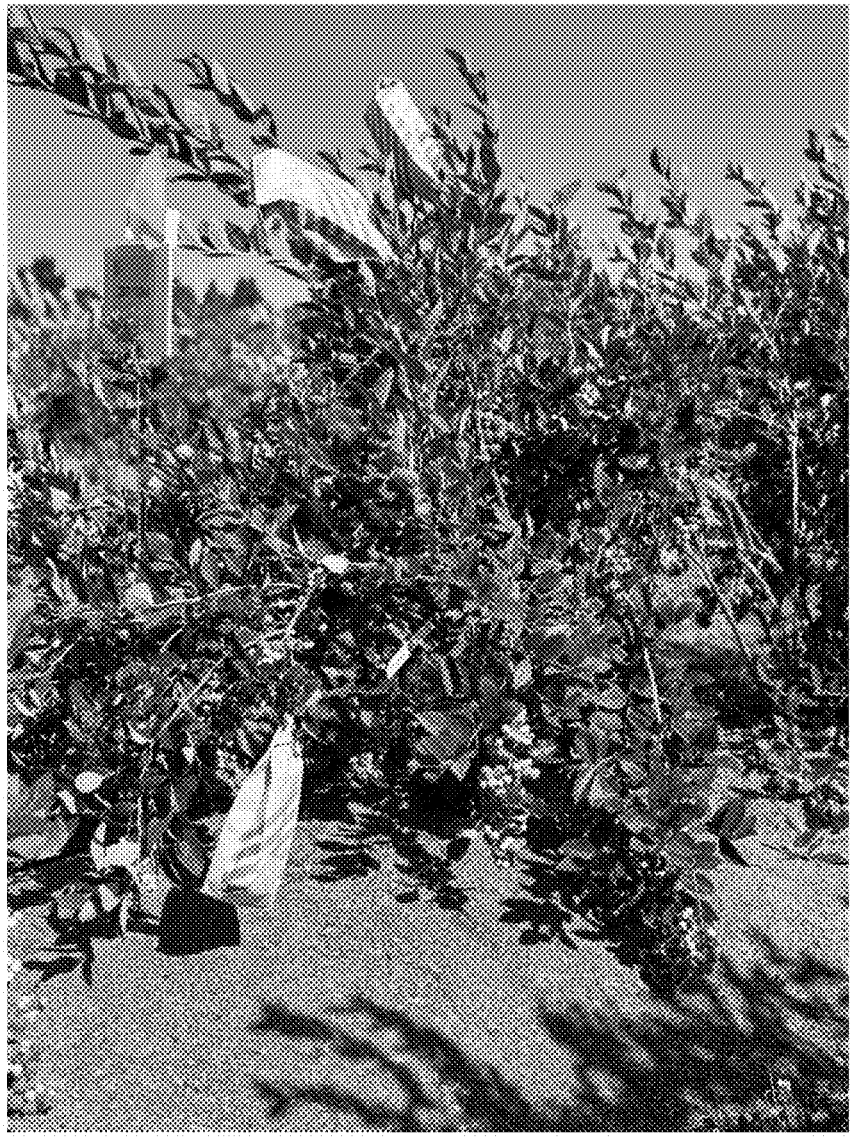
FIG. 2 is a photograph showing a five-year old 'OBG-18064' plant in ambient conditions outdoors in July 2025.
Figure 3:
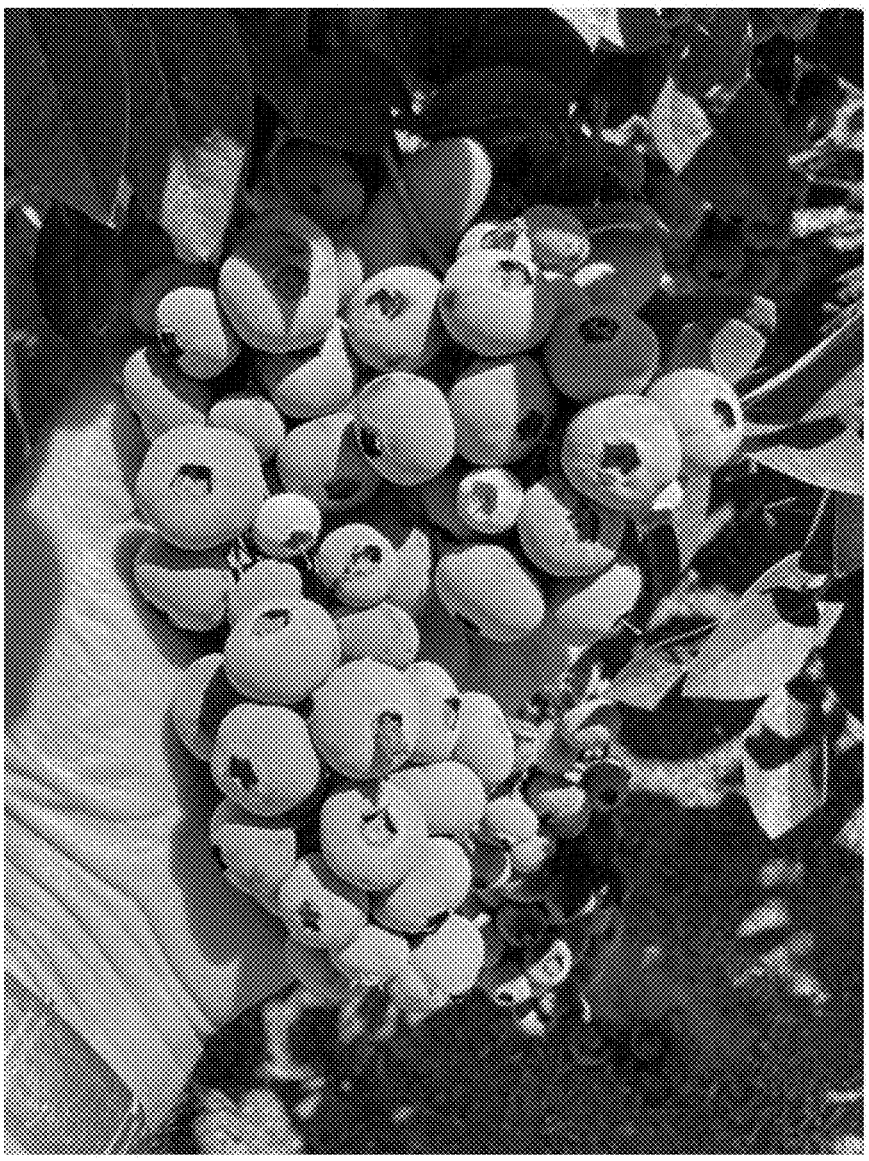
FIG. 3 is a photograph showing 'OBG-18064' fruit close-up on a 5 year-old plant in in ambient light conditions outdoors in July 2025.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

Color descriptions and other terminology in this application are used in accordance with their ordinary dictionary descriptions, unless the context clearly indicates otherwise. Color designations (hue/value/chroma) are made with reference to The Royal Horticultural Society Colour Chart (R.H.S.), 5$^{th}$ edition, London, England, 2007.

The following detailed description of 'OBG-18064' is based on observations of asexually reproduced progeny 6 years of age, which were grown in open fields with supplemental irrigation in Brooks, Oregon, USA. The average low temperature for the year ranges from 40-45° F. and the average high temperature of the year ranges from 90-95° F. The color values were determined in the 2025 growing season under natural light conditions in Brooks, Oregon, USA.

'OBG-18064' has not been observed under all environmental conditions. Certain characteristics of this variety may change with changing environmental conditions such as photoperiod, temperature, moisture, soil conditions, nutrient availability, or other factors. Thus, the phenotype may vary somewhat with variations in environmental conditions without any variance in the genotype.

Asexual reproduction of this new variety by vegetative cuttings show that the characteristics disclosed herein come true to form, are firmly fixed, and are established and transmitted through succeeding propagations.

Botanical classification: *Vaccinium corymbosum.*

Common name: Highbush blueberry.

Commercial classification: Fruit-bearing shrub.

Parentage:

*Female parent.*—'Bluecrop'.

*Male parent.*—Unknown, Open Pollination.

Plant:

*Growth habit.*—Semi-Erect, Bushy.

*Suckering.*—Moderate.

*Plant height.*—145.6 cm.

*Canopy diameter.*—146.6 cm.

*Vigor.*—Moderate High.

*Hardiness.*—USDA 5b-7b.

*Suitability for mechanical harvesting.*—Good.

*Deciduousness.*—Fully Deciduous.

*Time of beginning of leaf bud burst.*—April.

*One-year old canes.*—Length: 75 cm. Diameter at Base: 6.7 cm. Diameter at Tip: 2.7 cm. Texture: Smooth, Glaucous. Color: RHS 149B.

Foliage:

*Shape.*—Elliptic.

*Size.*—Length: 62 mm average. Width: 36 mm average.

*Leaf color.*—Spring Color: Upper Surface: RHS 137A tinted RHS 183B. Lower Surface: RHS 138B. Fall Color: Upper Surface: RHS 180A. Lower Surface: RHS 161D.

*Arrangement.*—Alternate.

*Leaf apices.*—Aristulate.

*Leaf bases.*—Cuneate.

*Leaf attitude.*—Ascending.

*Margin.*—Entire.

*Leaf texture.*—Upper Surface: Smooth, Glaucous. Lower Surface: Smooth, Glaucous.

*Venation pattern.*—Reticulate.

*Petiole.*—Length: 4.1 mm. Width: 1.5 mm. Color: RHS 145C. Surface Texture: Glaucous.

Wood texture:

*New wood* (*June/July*).—Smooth, Glaucous.

1 *yr wood* (*August*).—Smooth, Glaucous.

3 *yr. wood* (*August*).—Rough, Exfoliating.

Wood color:

*New wood* (*June/July*).—RHS 149B.

1 *yr. wood* (*August*).—RHS N144D.

3 *yr. wood* (*August*).—RHS N199A.

Wood buds:

*Average number of flower buds per fruiting lateral* (*in September*).—9.

Flowers:

*Flowering period.*—April-late May.

*Time of beginning of flowering.*—Early April.

*Time of* 50% *anthesis.*—April.

*Self*-compatibility.—95%.

*Fragrance.*—Light, Floral.

*Inflorescence size*.—Length: 15 cm. Width: 9 cm. Flowering Cluster Density: Moderate. Number of Flowers per Peduncle: 6.

*Flower buds*.—Immature Bud Color: RHS 4D. Mature Bud Color: RHS 4D. Bud Length: 13 mm. Bud Width: 6.8 mm.

*Flower pedicel*.—Color: RHS N144C. Length: 9.8 mm. Texture: Glaucous.

*Flower peduncle*.—Color: RHS N144C. Length: 31.9 mm average.

*Individual flower*.—Flower Shape: Urceolate. Flower Length: 14 mm. Protrusion of Stigma Beyond Corolla: 1.2 mm.

*Calyx* (*with sepals*).—Color: RHS 139D. Surface: Glaucous. Diameter: 4.4 mm average.

*Corolla*.—Color: RHS NN155D. Length: 9.6 mm. Width: 8 mm. Aperture/Width: 3.2 mm. Anthocyanin Coloration of Corolla at Time of Anthesis: Absent. Corolla Ridges: Present.

*Stamen*.—Length: 6.19 mm. Number: 10.Filament Color: RHS N144D. Filament Length: 3.69 mm.

*Anther*.—Length: 2.5 mm. Number: 10.Color: RHS N167A.

*Pollen*.—Abundance: Moderate. Color: RHS 155A.

*Pistil*.—Length: 14 mm. Ovary Color (exterior): RHS 138B. Style Length: 10.8 mm average. Ovary Depth: 3.2 mm.

Fruit:

*Time of fruit ripening*.—Mid June.

*Time of* 50% *maturity*.—Late June.

*Time of harvest*.—Early July.

*Fruit development period*.—70 days.

*Fruiting type*.—One year old and current season shoots.

*Cluster density*.—Moderate.

*Berries per cluster*.—Ranging from 5 to 10.

*Unripe berry color*.—RHS 142D.

*Unripe skin color after polishing*.—RHS 145A.

*Ripe berry color*.—RHS 98D.

*Ripe berry skin color after polishing*.—RHS 203C.

*Berry surface wax abundance*.—High.

*Berry flesh color*.—RHS 157D.

*Berry weight*.—4.3 g.

*Berry height from calyx to scar*.—14.5 mm.

*Berry diameter*.—20.8 mm average.

*Calyx aperture* (*mm*).—7.03 average.

*Calyx depth* (*mm*).—2.29 average.

*Pedicel length* (*mm*).—9.8 average.

*Pedicel surface texture*.—Smooth, glaucous.

*Berry attachment force*.—Moderate.

*Berry shape*.—Oblate.

*Fruit stem scar*.—Small, dry.

*Berry sweetness when ripe*.—13.0% soluble solids on average.

*Berry firmness when ripe*.—241.9 g/mm$^3$ average.

*Berry shelf life*.—Up to 4 weeks.

Seed:

*Seed color*.—RHS 175A.

*Seed length*.—1.7 mm average.

*Seed width*.—1.05 mm average.

*Seed dry weight*.—60 mg per 100 seeds.

*Quantity seeds per berry*.—19.

Disease/pest resistance:

*Stem blight* (*Botryosphaeria spp*.).—Undetermined.

*Root rot* (*Phytophthora cinnamomi*).—Does not appear to be overly susceptible.

*Phomopsis twig blight* (*Phomopsis vaccinii*).—Does not appear to be overly susceptible.

*Botryosphaeria stem canker* (*Botryosphaeria corticis*) .—Undetermined.

*Bacterial cane canker* (*Pseudomonas syringae*).—Does not appear to be overly susceptible.

*Botrytis blight* (*Botrytis cinerea*).—Does not appear to be overly susceptible.

*Leaf spot* (*Septoria spp*.).—Does not appear to be overly susceptible.

*Leaf rust* (*Naohidemyces vaccinii*).—Does not appear to be overly susceptible.

*Bud mites* (*Acalitus vaccinii*).—Undetermined.

Genetic Fingerprinting

2×4 mm leaf tissue punches were pooled together into a 2 ml tube. 1 cubic zirconia bead and 100 μl PVP lysis buffer was added. The sample was ground at 1400 RPM for 1 minute, after which 250 μl of additional PVP lysis buffer was added. The sample was incubated at 60° C. for 1 hour and DNA was extracted. Nine microsatellite markers (Marker 1-Marker 9) were then assayed by PCR reaction on the extracted DNA. The PCR product was diluted into a running buffer and subject to electrophoresis. Analysis was done using GeneMarker® software.

Variety differentiation is based on the amplified peaks of individual markers, which depend on the genetic makeup of the variety (See, e.g., Boches et al. "Genetic Diversity in the Highbush Blueberry Evaluated with Microsatellite Markers" *J. Amer. Soc. Hort. Sci.* 131(5):674-686, 2006). Each variety displays different peak patterns for each marker, creating a unique genetic "fingerprint." The unique genetic fingerprint for 'OBG-18064' is:

Marker 1: 290, 296, 299
Marker 2: 192
Marker 3: 219, 227
Marker 4: 192, 194
Marker 5: 110, 113, 116
Marker 6: 237, 244, 250
Marker 7: 374, 380
Marker 8: 321, 323, 324, 332
Marker 9: 106, 109, 112

TABLE 2

Primer pairs for marker detection.

| Marker # | Forward | Reverse |
|---|---|---|
| 1 | TCCTCGTTCTCTCCCTCTCA (SEQ ID NO: 1) | CGCTGAAGTTGGAGTCCTT (SEQ ID NO: 2) |
| 2 | TCAGACATGATTGGGGAGGT (SEQ ID NO: 3) | GGAATAATAGAGGCGGTGGA (SEQ ID NO: 4) |
| 3 | GTTAAGCTTTTAGATGAGTTG ATGG (SEQ ID NO: 5) | AACCAGTCCCAGACCCAAAT (SEQ ID NO: 6) |
| 4 | CGCAATCGCTGCATAGTTTA (SEQ ID NO: 7) | GTTTAACGTTGCAACCAATTC CA (SEQ ID NO: 8) |
| 5 | TAGTGGAGGGTTTTGCTTGG (SEQ ID NO: 9) | ATCGAAGCGAAGGTCAAAGA (SEQ ID NO: 10) |
| 6 | CGCGTGAAAAACGACCTAAT (SEQ ID NO: 11) | ACTCGATCCCTCCACCTG (SEQ ID NO: 12) |

TABLE 2-continued

Primer pairs for marker detection.

| Marker # | Forward | Reverse |
|---|---|---|
| 7 | CACCCATTTCACGGAATCTC (SEQ ID NO: 13) | ACTTGGTCGGGTGTTGTCTC (SEQ ID NO: 14) |
| 8 | TCTCTTTCCCTTTTCAAGTGG (SEQ ID NO: 15) | GTTTATGATGGAATTCCGAGTTTG (SEQ ID NO: 16) |

TABLE 2-continued

Primer pairs for marker detection.

| Marker # | Forward | Reverse |
|---|---|---|
| 9 | GTTCATCCCAATGCAGAAGAAG (SEQ ID NO: 17) | GTTTCCTCTTGTGGGTTAGGGTTTCT (SEQ ID NO: 18) |

SEQUENCE LISTING

```
Sequence total quantity: 18
SEQ ID NO: 1            moltype = DNA  length = 20
FEATURE                 Location/Qualifiers
source                  1..20
                        mol_type = other DNA
                        organism = synthetic construct
SEQUENCE: 1
tcctcgttct ctccctctca                                              20

SEQ ID NO: 2            moltype = DNA  length = 19
FEATURE                 Location/Qualifiers
source                  1..19
                        mol_type = other DNA
                        organism = synthetic construct
SEQUENCE: 2
cgctgaagtt ggagtcctt                                               19

SEQ ID NO: 3            moltype = DNA  length = 20
FEATURE                 Location/Qualifiers
source                  1..20
                        mol_type = other DNA
                        organism = synthetic construct
SEQUENCE: 3
tcagacatga ttggggaggt                                              20

SEQ ID NO: 4            moltype = DNA  length = 20
FEATURE                 Location/Qualifiers
source                  1..20
                        mol_type = other DNA
                        organism = synthetic construct
SEQUENCE: 4
ggaataatag aggcggtgga                                              20

SEQ ID NO: 5            moltype = DNA  length = 25
FEATURE                 Location/Qualifiers
source                  1..25
                        mol_type = other DNA
                        organism = synthetic construct
SEQUENCE: 5
gttaagcttt tagatgagtt gatgg                                        25

SEQ ID NO: 6            moltype = DNA  length = 20
FEATURE                 Location/Qualifiers
source                  1..20
                        mol_type = other DNA
                        organism = synthetic construct
SEQUENCE: 6
aaccagtccc agacccaaat                                              20

SEQ ID NO: 7            moltype = DNA  length = 20
FEATURE                 Location/Qualifiers
source                  1..20
                        mol_type = other DNA
                        organism = synthetic construct
SEQUENCE: 7
cgcaatcgct gcatagttta                                              20

SEQ ID NO: 8            moltype = DNA  length = 23
FEATURE                 Location/Qualifiers
source                  1..23
                        mol_type = other DNA
                        organism = synthetic construct
SEQUENCE: 8
```

-continued

```
gtttaacgtt gcaaccaatt cca                                          23

SEQ ID NO: 9            moltype = DNA  length = 20
FEATURE                 Location/Qualifiers
source                  1..20
                        mol_type = other DNA
                        organism = synthetic construct
SEQUENCE: 9
tagtggaggg ttttgcttgg                                              20

SEQ ID NO: 10           moltype = DNA  length = 20
FEATURE                 Location/Qualifiers
source                  1..20
                        mol_type = other DNA
                        organism = synthetic construct
SEQUENCE: 10
atcgaagcga aggtcaaaga                                              20

SEQ ID NO: 11           moltype = DNA  length = 20
FEATURE                 Location/Qualifiers
source                  1..20
                        mol_type = other DNA
                        organism = synthetic construct
SEQUENCE: 11
cgcgtgaaaa acgacctaat                                              20

SEQ ID NO: 12           moltype = DNA  length = 18
FEATURE                 Location/Qualifiers
source                  1..18
                        mol_type = other DNA
                        organism = synthetic construct
SEQUENCE: 12
actcgatccc tccacctg                                                18

SEQ ID NO: 13           moltype = DNA  length = 20
FEATURE                 Location/Qualifiers
source                  1..20
                        mol_type = other DNA
                        organism = synthetic construct
SEQUENCE: 13
cacccatttc acggaatctc                                              20

SEQ ID NO: 14           moltype = DNA  length = 20
FEATURE                 Location/Qualifiers
source                  1..20
                        mol_type = other DNA
                        organism = synthetic construct
SEQUENCE: 14
acttggtcgg gtgttgtctc                                              20

SEQ ID NO: 15           moltype = DNA  length = 21
FEATURE                 Location/Qualifiers
source                  1..21
                        mol_type = other DNA
                        organism = synthetic construct
SEQUENCE: 15
tctctttccc ttttcaagtg g                                            21

SEQ ID NO: 16           moltype = DNA  length = 22
FEATURE                 Location/Qualifiers
source                  1..22
                        mol_type = other DNA
                        organism = synthetic construct
SEQUENCE: 16
gtttatgatg gaattccgag tt                                           22

SEQ ID NO: 17           moltype = DNA  length = 22
FEATURE                 Location/Qualifiers
source                  1..22
                        mol_type = other DNA
                        organism = synthetic construct
SEQUENCE: 17
gttcatccca atgcagaaga ag                                           22

SEQ ID NO: 18           moltype = DNA  length = 26
FEATURE                 Location/Qualifiers
source                  1..26
                        mol_type = other DNA
```

-continued

```
                    organism = synthetic construct
SEQUENCE: 18
gtttcctctt gtgggttagg gtttct                                    26
```

I claim:

1. A new and distinct variety of blueberry plant named 'OBG-18064', substantially as illustrated and described herein.

* * * * *